US010654219B2

(12) United States Patent
Hodgdon et al.

(10) Patent No.: US 10,654,219 B2
(45) Date of Patent: May 19, 2020

(54) METHOD FOR MANUFACTURING A THREE-DIMENSIONAL OBJECT

(71) Applicant: The Procter & Gamble Company, Cincinnati, OH (US)

(72) Inventors: Travis Kyle Hodgdon, Cincinnati, OH (US); Freddy Arthur Barnabas, West Chester, OH (US); Michael Sean Farrell, Terrace Park, OH (US); Charles John Berg, Jr., Wyoming, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 254 days.

(21) Appl. No.: 15/670,198

(22) Filed: Aug. 7, 2017

(65) Prior Publication Data

US 2018/0065310 A1 Mar. 8, 2018

Related U.S. Application Data

(60) Provisional application No. 62/384,316, filed on Sep. 7, 2016.

(51) Int. Cl.
B29C 64/118 (2017.01)
A61K 8/02 (2006.01)
A61K 9/00 (2006.01)
A61K 6/15 (2020.01)
B29C 64/165 (2017.01)
B33Y 10/00 (2015.01)
B33Y 50/02 (2015.01)
B33Y 70/00 (2020.01)
B29C 64/393 (2017.01)
C08K 3/36 (2006.01)
C08K 5/1545 (2006.01)
C08L 3/02 (2006.01)
C08L 5/00 (2006.01)
C08L 71/00 (2006.01)
C11B 9/00 (2006.01)
B29K 71/00 (2006.01)
B29K 105/16 (2006.01)
B29K 509/00 (2006.01)

(52) U.S. Cl.
CPC ............ B29C 64/118 (2017.08); A61K 6/15 (2020.01); A61K 8/02 (2013.01); A61K 9/00 (2013.01); B29C 64/165 (2017.08); B29C 64/393 (2017.08); B33Y 10/00 (2014.12); B33Y 50/02 (2014.12); B33Y 70/00 (2014.12); C08K 3/36 (2013.01); C08K 5/1545 (2013.01); C08L 3/02 (2013.01); C08L 5/00 (2013.01); C08L 71/00 (2013.01); C11B 9/00 (2013.01); B29K 2071/00 (2013.01); B29K 2071/02 (2013.01); B29K 2105/16 (2013.01); B29K 2403/00 (2013.01); B29K 2405/00 (2013.01); B29K 2509/00 (2013.01); B29K 2995/0062 (2013.01)

(58) Field of Classification Search
CPC .................................................. B29C 64/118
See application file for complete search history.

(56) References Cited

U.S. PATENT DOCUMENTS

| | | | | |
|---|---|---|---|---|
| 8,158,571 | B2 * | 4/2012 | Alonso | C11D 3/3715 510/441 |
| 8,696,975 | B2 * | 4/2014 | Ylitalo | A01N 25/34 264/496 |
| 10,413,758 | B2 * | 9/2019 | Jaunet | A61Q 19/10 |
| 10,543,639 | B2 * | 1/2020 | Hodgdon | B33Y 10/00 |
| 2017/0232675 | A1 * | 8/2017 | Jaunet | A61Q 5/02 264/494 |
| 2017/0232676 | A1 * | 8/2017 | Jaunet | B33Y 10/00 264/308 |
| 2017/0361495 | A1 * | 12/2017 | Schamp | B33Y 80/00 |
| 2017/0361496 | A1 * | 12/2017 | Schamp | B29B 9/12 |
| 2018/0110250 | A1 * | 4/2018 | Popplewell | A61K 8/8129 |
| 2018/0334642 | A1 * | 11/2018 | Hodgdon | C11D 17/047 |
| 2019/0002172 | A1 * | 1/2019 | Hodgdon | B33Y 80/00 |
| 2019/0309163 | A1 * | 10/2019 | Hodgdon | C11D 3/3726 |
| 2019/0309238 | A1 * | 10/2019 | Hodgdon | C11D 1/143 |
| 2020/0086551 | A1 * | 3/2020 | Hodgdon | A61Q 19/00 |

OTHER PUBLICATIONS

Kutikov, Artem B., and Jie Song. "Biodegradable PEG-based amphiphilic block copolymers for tissue engineering applications." ACS biomaterials science & engineering 1.7 (May 26, 2015): 463-480. (Year: 2015).*
Yow, Huai Nyin, and Alexander F. Routh. "Formation of liquid core-polymer shell microcapsules." Soft Matter 2.11 (Aug. 29, 2006): 940-949. (Year: 2006).*
International Search Report and Written Opinion, U.S. Appl. No. 15/670,198, dated Oct. 5, 2017, 9 pages.
Hoque et al, "Fabrication and characterization of hybrid PCL/PEG 3D scaffolds for potential tissue engineering application", Materials Letters, vol. 131, 2014, pp. 255-258, XP028875877, ISSN: 0167-577X.

(Continued)

Primary Examiner — Benjamin A Schiffman
(74) Attorney, Agent, or Firm — Alexandra S. Anoff

(57) ABSTRACT

A method for manufacturing a three-dimensional object includes steps of: a) providing a digital description of the object as a set of voxels; b) sequentially creating an actual set of voxels corresponding to the digital set of voxels; wherein at least one voxel comprises a composition comprising between about 35 and about 100 wt. % of a polymer selected from the group consisting of nonionic PEG homopolymers, PEG copolymers, and mixtures thereof; the polymer having an average molecular weight of between about 1,000 and about 95,000 AMU; and between about 0 and about 65 wt. % of a filler, wherein the filler is a solid at a temperature of above about 75 C, wherein the composition has a Melt Flow Index of between about 0.1 and about 50 g/10 min when measured at 70 C under a 1.2 kg load using a half-die according to ASTM D1238-13.

15 Claims, No Drawings
Specification includes a Sequence Listing.

(56) References Cited

OTHER PUBLICATIONS

Hoque et al, "Processing of Polycaprolactone-Based Copolymers into 3D Scaffolds, and Their Cellular Responses", Tissue Engineering Part A, vol. 15, No. 10, Oct. 1, 2009, pp. 3013-3024, XP055412724, ISSN: 1937-3341.

* cited by examiner

```
                        SEQUENCE LISTING

<160> NUMBER OF SEQ ID NOS: 1

<210> SEQ ID NO 1
<211> LENGTH: 773
<212> TYPE: PRT
<213> ORGANISM: Bacillus sp.

<400> SEQUENCE: 1

Ala Glu Gly Asn Thr Arg Glu Asp Asn Phe Lys His Leu Leu Gly Asn
1               5                   10                  15

Asp Asn Val Lys Arg Pro Ser Glu Ala Gly Ala Leu Gln Leu Gln Glu
            20                  25                  30

Val Asp Gly Gln Met Thr Leu Val Asp Gln His Gly Glu Lys Ile Gln
        35                  40                  45

Leu Arg Gly Met Ser Thr His Gly Leu Gln Trp Phe Pro Glu Ile Leu
    50                  55                  60

Asn Asp Asn Ala Tyr Lys Ala Leu Ala Asn Asp Trp Glu Ser Asn Met
65                  70                  75                  80

Ile Arg Leu Ala Met Tyr Val Gly Glu Asn Gly Tyr Ala Ser Asn Pro
                85                  90                  95

Glu Leu Ile Lys Ser Arg Val Ile Lys Gly Ile Asp Leu Ala Ile Glu
            100                 105                 110

Asn Asp Met Tyr Val Ile Val Asp Trp His Val His Ala Pro Gly Asp
            115                 120                 125

Pro Arg Asp Pro Val Tyr Ala Gly Ala Glu Asp Phe Phe Arg Asp Ile
        130                 135                 140

Ala Ala Leu Tyr Pro Asn Asn Pro His Ile Ile Tyr Glu Leu Ala Asn
145                 150                 155                 160

Glu Pro Ser Ser Asn Asn Gly Gly Ala Gly Ile Pro Asn Asn Glu
                165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Ile Val Gly Ser
        195                 200                 205

Pro Asn Trp Ser Gln Arg Pro Asp Leu Ala Ala Asp Asn Pro Ile Asn
    210                 215                 220

Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
                245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Asn Gly Asp Gly Gly Pro
        275                 280                 285

Tyr Phe Asp Glu Ala Asp Val Trp Ile Glu Phe Leu Asn Glu Asn Asn
    290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Asn Leu Asp
                325                 330                 335
```

```
Pro Gly Pro Asp His Val Trp Ala Pro Glu Leu Ser Leu Ser Gly
        340                 345                 350
Glu Tyr Val Arg Ala Arg Ile Lys Gly Val Asn Tyr Glu Pro Ile Asp
            355                 360                 365
Arg Thr Lys Tyr Thr Lys Val Leu Trp Asp Phe Asn Asp Gly Thr Lys
        370                 375                 380
Gln Gly Phe Gly Val Asn Ser Asp Ser Pro Asn Lys Glu Leu Ile Ala
385                 390                 395                 400
Val Asp Asn Glu Asn Asn Thr Leu Lys Val Ser Gly Leu Asp Val Ser
            405                 410                 415
Asn Asp Val Ser Asp Gly Asn Phe Trp Ala Asn Ala Arg Leu Ser Ala
            420                 425                 430
Asp Gly Trp Gly Lys Ser Val Asp Ile Leu Gly Ala Glu Lys Leu Thr
            435                 440                 445
Met Asp Val Ile Val Asp Glu Pro Thr Thr Val Ala Ile Ala Ala Ile
        450                 455                 460
Pro Gln Ser Ser Lys Ser Gly Trp Ala Asn Pro Glu Arg Ala Val Arg
465                 470                 475                 480
Val Asn Ala Glu Asp Phe Val Gln Gln Thr Asp Gly Lys Tyr Lys Ala
            485                 490                 495
Gly Leu Thr Ile Thr Gly Glu Asp Ala Pro Asn Leu Lys Asn Ile Ala
        500                 505                 510
Phe His Glu Glu Asp Asn Asn Met Asn Asn Ile Ile Leu Phe Val Gly
        515                 520                 525
Thr Asp Ala Ala Asp Val Ile Tyr Leu Asp Asn Ile Lys Val Ile Gly
        530                 535                 540
Thr Glu Val Glu Ile Pro Val Val His Asp Pro Lys Gly Glu Ala Val
545                 550                 555                 560
Leu Pro Ser Val Phe Glu Asp Gly Thr Arg Gln Gly Trp Asp Trp Ala
                565                 570                 575
Gly Glu Ser Gly Val Lys Thr Ala Leu Thr Ile Glu Glu Ala Asn Gly
            580                 585                 590
Ser Asn Ala Leu Ser Trp Glu Phe Gly Tyr Pro Glu Val Lys Pro Ser
        595                 600                 605
Asp Asn Trp Ala Thr Ala Pro Arg Leu Asp Phe Trp Lys Ser Asp Leu
        610                 615                 620
Val Arg Gly Glu Asn Asp Tyr Val Ala Phe Asp Phe Tyr Leu Asp Pro
625                 630                 635                 640
Val Arg Ala Thr Glu Gly Ala Met Asn Ile Asn Leu Val Phe Gln Pro
            645                 650                 655
Pro Thr Asn Gly Tyr Trp Val Gln Ala Pro Lys Thr Tyr Thr Ile Asn
        660                 665                 670
Phe Asp Glu Leu Glu Glu Ala Asn Gln Val Asn Gly Leu Tyr His Tyr
        675                 680                 685
Glu Val Lys Ile Asn Val Arg Asp Ile Thr Asn Ile Gln Asp Asp Thr
        690                 695                 700
Leu Leu Arg Asn Met Met Ile Ile Phe Ala Asp Val Glu Ser Asp Phe
705                 710                 715                 720
Ala Gly Arg Val Phe Val Asp Asn Val Arg Phe Glu Gly Ala Ala Thr
            725                 730                 735
Thr Glu Pro Val Glu Pro Glu Pro Val Asp Pro Gly Glu Thr Pro
        740                 745                 750
```

```
Pro Val Asp Glu Lys Glu Ala Lys Lys Glu Gln Lys Glu Ala Glu Lys
        755                 760                 765

Glu Glu Lys Glu Glu
    770
```

METHOD FOR MANUFACTURING A THREE-DIMENSIONAL OBJECT

FIELD OF THE INVENTION

The invention relates to methods for manufacturing articles from polymeric materials. The invention relates particularly to manufacturing water soluble articles from modified polyethylene glycol materials as a sequence of voxels.

BACKGROUND OF THE INVENTION

Manufacturing articles from polymeric materials is well known in the technological arts. Manufacturing articles as a presented sequence of volume elements (voxels) derived from a digital representation of an article is also well known. That some envisioned articles may have greater utility depending upon the extent to which at least portions of the respective articles are water soluble can be envisioned. Water soluble polymers are not generally dimensionally stable enough to enable the manufacturing of objects on a voxel-by-voxel basis without a material constraining mold or support structure. In addition to dimensional stability, the ability to adjust or tune the rate at which an article dissolves when in use, and the ability to process the material into an article at temperatures at or below the respective boiling points of carrier solvents such as water and alcohol, is also beneficial to preserve the nature of temperature sensitive benefit agents. What is needed is a polymeric material which is both dimensionally stable enough to enable the creation of objects by fabricating a series of voxels according to a digital representation of the desired object at temperatures which preserve the utility of benefit agents, as well as soluble in an aqueous environment to yield the desired advanced utility; and a method for manufacturing articles from such a material.

SUMMARY OF THE INVENTION

In one aspect, a method for manufacturing a three-dimensional object includes steps of: a) providing a digital description of the object as a set of voxels; b) sequentially creating an actual set of voxels corresponding to the digital set of voxels; wherein at least one voxel comprises a composition comprising between about 35 and about 100 wt. % of a polymer selected from the group consisting of nonionic polyethylene glycol (PEG) homopolymers, PEG copolymers, and mixtures thereof; the polymer having an average molecular weight of between about 1,000 and about 95,000 AMU; and between about 0 and about 65 wt. % of a filler, wherein the filler is a solid at a temperature of above about 75 C, wherein the composition has a Melt Flow Index of between about 0.1 g/10 minutes and about 50 g/10 minutes when tested in accordance with ASTM D1238-13 under a 1.2 kg load at 70 C using a half-die.

In one aspect, an article comprises between about 35 and about 100 wt. % of a polymer selected from the group consisting of nonionic polyethylene glycol PEG homopolymers, PEG copolymers, and mixtures thereof; the polymer having an average molecular weight of between about 1,000 and about 95,000 AMU; and between about 0 and about 65 wt. % of a filler, wherein the filler is a solid at a temperature of above about 75 C, wherein the composition has a Melt Flow Index of between about 0.1 g/10 minutes and about 50 g/10 minutes when tested in accordance with ASTM D1238-13 under a 1.2 kg load at 70 C using a half-die.

In one aspect, a composition between about 35 and about 99 wt. % of a polymer selected from the group consisting of nonionic polyethylene glycol PEG homopolymers, PEG copolymers, and mixtures thereof; the polymer having an average molecular weight of between about 1,000 and about 95,000 AMU; and between about 0 and about 65 wt. % of a filler, wherein the filler is a solid at a temperature of above about 75 C, wherein the composition has a Melt Flow Index of between about 0.1 g/10 minutes and about 50 g/10 minutes when tested in accordance with ASTM D1238-13 under a 1.2 kg load at 70 C using a half-die.

DETAILED DESCRIPTION OF THE INVENTION

In one embodiment, the method for manufacturing a three-dimensional object includes steps of: a) providing a digital description of the object as a set of voxels; b) sequentially creating an actual set of voxels corresponding to the digital set of voxels; wherein at least one voxel comprises a composition comprising between about 35 and about 100 wt. % of a polymer selected from the group consisting of nonionic PEG homopolymers, PEG copolymers, and mixtures thereof; the polymer having an average molecular weight of between about 1,000 and about 95,000 AMU; and between about 0 and about 65 wt. % of a filler, wherein the filler is a solid at a temperature of above about 75 C, wherein the composition has a Melt Flow Index of between about 0.1 g/10 minutes and about 50 g/10 minutes when tested in accordance with ASTM D1238-13 under a 1.2 kg load at 70 C using a half die.

In one embodiment, the composition comprises between about 35 and about 99 wt. % of a polymer selected from the group consisting of nonionic PEG homopolymers, PEG copolymers, and mixtures thereof; the polymer having an average molecular weight of between about 1,000 and about 95,000 AMU; and between about 1 and about 65 wt. % of a filler, wherein the filler is a solid at a temperature of above about 75 C, wherein the composition has a Melt Flow Index of between about 0.1 g/10 minutes and about 50 g/10 minutes when tested in accordance with ASTM D1238-13 under a 1.2 kg load at 70 C using a half die.

In one embodiment, the composition comprises between about 35 and about 100 wt. % of a polymer selected from the group consisting of nonionic PEG homopolymers, PEG copolymers, and mixtures thereof; the polymer having an average molecular weight of between about 1,000 and about 95,000 AMU; and between about 0 and about 65 wt. % of a filler, wherein the filler is a solid at a temperature of above about 75 C, wherein the composition has a Melt Flow Index of between about 0.1 g/10 minutes and about 50 g/10 minutes when tested in accordance with ASTM D1238-13 under a 1.2 kg load at 70 C using a half die.

In one embodiment, the composition comprises between about 40 and about 96 wt. % of a polymer selected from the group consisting of nonionic PEG homopolymers, PEG copolymers, and mixtures thereof; the polymer having an average molecular weight of between about 1,000 and about 95,000 AMU; and between about 4 and about 60 wt. % of a filler, wherein the filler is a solid at a temperature of above about 75 C, wherein the composition has a Melt Flow Index of between about 0.1 g/10 minutes and about 50 g/10 minutes when tested in accordance with ASTM D1238-13 under a 1.2 kg load at 70 C using a half die.

In one embodiment, the composition comprises between about 50 and about 94 wt. % of a polymer selected from the group consisting of nonionic PEG homopolymers, PEG copolymers, and mixtures thereof; the polymer having an average molecular weight of between about 1,000 and about 95,000 AMU; and between about 6 and about 50 wt. % of a filler, wherein the filler is a solid at a temperature of above about 75 C, wherein the composition has a Melt Flow Index of between about 0.1 g/10 minutes and about 50 g/10 minutes when tested in accordance with ASTM D1238-13 under a 1.2 kg load at 70 C using a half die.

In one embodiment, the composition comprises between about 55 and about 92 wt. % of a polymer selected from the group consisting of nonionic PEG homopolymers, PEG copolymers, and mixtures thereof; the polymer having an average molecular weight of between about 1,000 and about 95,000 AMU; and between about 8 and about 45 wt. % of a filler, wherein the filler is a solid at a temperature of above about 75 C, wherein the composition has a Melt Flow Index of between about 0.1 g/10 minutes and about 50 g/10 minutes when tested in accordance with ASTM D1238-13 under a 1.2 kg load at 70 C using a half die.

In one embodiment, the composition comprises between about 70 and about 80 wt. % of a polymer selected from the group consisting of nonionic PEG homopolymers, PEG copolymers, and mixtures thereof; the polymer having an average molecular weight of between about 1,000 and about 95,000 AMU; and between about 20 and about 30 wt. % of a filler, wherein the filler is a solid at a temperature of above about 75 C, wherein the composition has a Melt Flow Index of between about 0.1 g/10 minutes and about 50 g/10 minutes when tested in accordance with ASTM D1238-13 under a 1.2 kg load at 70 C using a half die.

The digital description of the object as a set of voxels may be the result of a digital design process using computer aided design software to create a representation of the object. In one embodiment, the digital description may be result of scanning an object to create a digital representation of the object. The initial scanning of the object may result in a digital file which may be enhanced or otherwise altered using appropriate software. In one embodiment, a set of two dimensional images may be interpolated to yield a three dimensional representation of the object as an array or sequence of voxels. The digital description may be provided as a .stl or other known file format.

The provided digital description may be translated to an actual object by the creation of an actual set of voxels corresponding to the set of voxels in the digital representation. This translation may be accomplished using known additive manufacturing techniques including material extrusion techniques, and those techniques referred to as 3D printing, or three dimensional printing techniques. Exemplary apparatus for the translation include fused deposition modeling (FDM) where each digital voxel is translated to an actual voxel by depositing a single liquid drop of material from a nozzle onto a build platform that freezes, cures or hardens to form the actual voxel. The nozzle and/or build-platform move to allow for at least three dimensions of orthogonal motion relative to one another. Voxels are typically deposited to form a two dimensional layer and then another layer of fluid material is deposited over the preceding layer to form the three dimensional object. The liquid droplet size and the distance between the dispensing nozzle and the proceeding layer control voxel size. Material for extrusion through the nozzle may be in a filament, pellet, powder or liquid form. A plurality of build materials may be used. It is preferred that the build-platform, nozzle and any liquid reservoir is temperature controlled. A fan may be used to aid in cooling of extruded material The final object may be post processed using any known methods including sanding, polishing and steaming to improve surface finish.

In one embodiment, each voxel of the set of voxels of the actual article is comprised of substantially the same material as all other voxels of the set. Alternatively, respective portions of the overall set of voxels may be comprised of differing materials.

At least one voxel of the set of voxels in the actual object resulting from the translation, comprises between about 35 and about 100 weight percent (wt. %) polymer. The polymer may be selected from the group consisting of nonionic PEG homopolymers, PEG copolymers, and mixtures thereof. The polymer having an average molecular weight of between about 1,000 and about 95,000 AMU. Exemplary PEG homopolymers include: polyethylene glycol available from Sigma Aldrich, CARBOWAX™ available from Dow, and Pluriol® available from BASF. Exemplary PEG copolymers include Pluronic® available from BASF, poly(lactide-block-ethylene glycol), poly(glycolide-block-ethylene glycol), poly(lactide-co-caprolactone)-block-poly(ethylene glycol), poly(ethylene glycol-co-lactic acid), poly(ethylene glycol-co-glycolic acid), poly(ethylene glycol-co-poly(lactic acid-co-glycolic acid), poly(ethylene glycol-co-propylene glycol), poly(ethylene oxide-block-propylene oxide-block-ethylene oxide), poly(propylene oxide-block-ethylene glycol-block-propylene glycol), and poly(ethylene glycol-co-caprolactone). The polymers may be linear, branched, cross-linked, dendritic, or star polymers. PEG copolymers may be random, block, comb, or graft copolymers.

In one embodiment, the polymer comprises at least about 50 wt. % PEG having an average molecular weight of between about 1,000 and about 95,000 AMU.

The voxel further comprises between about 0 and about 65 weight percent (wt. %) of a filler, wherein the filler is a solid at a temperature of above about 75 C, and solid at temperatures greater than the melting, processing and printing temperature of the overall composition. Fillers may be organic, inorganic or of mixed inorganic/organic nature. Suitable fillers are selected from the group consisting of: starches, gums, proteins, amino acids, water soluble polymers, water degradable polymers, water insoluble polymers, sugars, sugar alcohols, inorganic particles, surfactants, fatty amphiphiles and mixtures thereof.

Starches may be sourced from plant materials including: corn, wheat, potato, rice, cassava and tapioca. Starches may be unmodified, modified, or partially degraded. Modified starch may include cationic starch, hydroxyehtyl starch, carboxymethylated starch, and polylactic acid graft-starch and polycaprylactone graft starch. Degraded starches may include dextrin and maltodextrin preferably with a dextrose equivalent of 30 or lower.

Gums can be extracted from natural sources, modified from natural sources or fermented. Suitable natural sources from gums include trees, plants, animals and seeds. Examples of natural gums include gum acacia, gum tragacanth, gum karaya, gum ghatti, nanocrylstalline cellulose, pectin, carrageenan, agar, furcellaran, konjac gum, gelatin, guar gum, locust bean gum, tara gum, cassia gum, mesquite gum, tamarind seed gum, quince seed gum, flaxseed gum, phyllium seed gum, oat gum, and microfibrillated cellulose. Gums may also be modified to create alkali cellulose, salts of carboxymethylcellulose, methylcellulose, hydroxypropyl methylcellulose, and hydroxypropyl cellulose. Examples of fermented gums are xanthan gum, dextran and pullulan.

Suitable water-soluble polymers may be synthesized using vinyl addition reaction or ring opening synthesis. Examples of vinyl addition polymers are polyvinyl alcohol, poly(acrylic acid), poly(methacrylic acid), Poly(2-dimethylamino ethyl methacrylate) methyl chloride quaternary salt, Poly(2-dimethylamino ethylacrylate) methyl chloride quaternary salt, poly(allylamine), polyacrylamide, polymethacrylamide, poly[n-(2-hydroxypropyl) methacrylamide], Poly((3-acrylamidopropyl)trimethylammonium chloride), poly(n-(2-aminoethyl) methacrylamide hydrochloride quantized salt), poly(N-isopropylacrylamide), polyvinylpyrrolidone, poly(diallyl dimethyl ammonium chloride), poly(styrenesulfonic acid), and poly(vinyl phosphoric acid). Examples of ring opening synthesized polymers include poly(2-oxazoline), poly(2-ethyl-2-oxazoline), polyethyleneimine, poly(maleic anhydride), and polyaspartic acid. Water soluble copolymers such as poly(vinyl alcohol)-co-poly(ethylene glycol) available as Kollicoat® from BASF.

Water degradable polymers typically contain an ester bond in their backbone leading to hydrolysis in water. Examples of water degradable polymers are polylactic acid, polyglycolic acid, polybutylene succinate, polycaprolactone, polybutyrate, and poly(glycolic acid-co-lactic acid).

Examples of water insoluble polymers include nylon, polystyrene, polyurethane, polyvinyl chloride, polytetrafluoroethylene, latex and polyethylene. Latex may be natural rubber or synthetic. Commonly available synthetic latexes include nitrile rubber, polychloroprene, butyl rubber, fluorocarbon rubber, polyurethane, styrene-butadiene rubber and blends thereof. Polyethylene particles are available under the tradename VELUSTROL from HOECHST Aktiengesellschaft of Frankfurt am Main, Germany.

Examples of sugars and sugar alcohols include glucose, fructose, galactose, sucrose, maltose, lactose and trehalose. Examples of sugar alcohols include erythritol, threitol, arabitol, ribitol, xylitol, mannitol, sorbitol, galactitol, iditol, volemitol, fucitol, inositol, maltitol and lactitol. Examples of inorganic particles include silica, fumed silica, precipitated silica, talcum powder, graphite, aluminum oxide, iron oxide, antimony trioxide, copper, bentonite clay, laponite clay, aluminium silicate clay, calcium carbonate, sodium chloride, magnesium chloride, calcium chloride, tetramethyl ammonium chloride, alumina, titanium dioxide, chalk, titanium hydroxide, gypsum powder and sodium sulfate.

Examples of organic salts include choline chloride, betaine, sorbic acid, and uric acid.

Examples of surfactants can be cationic, anionic, nonionic or zwitterinoic and include sodium dodecyl sulfate, sodium dodecylbenzenesulfonate, glucose amide, cetyl and trimethylammonium bromide.

Examples of fatty amphiphiles are fatty alcohols, alkoxylated fatty alcohols, fatty phenols, alkoxylated fatty phenols, fatty amides, alkyoxylated fatty amides, fatty amines, fatty alkylamidoalkylamines, fatty alkyoxyalted amines, fatty carbamates, fatty amine oxides, fatty acids, alkoxylated fatty acids, fatty diesters, fatty sorbitan esters, fatty sugar esters, methyl glucoside esters, fatty glycol esters, mono-, di- and tri-glycerides, polyglycerine fatty esters, alkyl glyceryl ethers, propylene glycol fatty acid esters, cholesterol, ceramides, fatty silicone waxes, fatty glucose amides, and phospholipids.

Mixtures of fillers may be used. These mixtures can be physical blends of two or more types of fillers or two or more fillers that are melted or dissolved together to form a single filler comprising two or more materials. Suitable methods for forming filler particles include any typical method for creating powders such as grinding, milling, spray drying, roll drying, and prilling.

Every dimension of the filler particles should be smaller than the FDM printer nozzle diameter, more preferably less than 0.5 times and more preferably less than 0.1 times the FDM printer nozzle diameter. The size of filler particles can be reduced by any common method for segregating or reducing particle size including sieving, grinding, cryogenic grinding, and milling. Size and shape of the filler particles can be determined by common means such as sieving through a series of mesh screens or laser diffraction. In one embodiment, the filler particles are spherical or ellipsoidal in shape. Exemplary filler particles are spherical in shape.

The melting temperature of the filler particle must be greater than the melting, processing and printing temperatures of the final mixture. Melting temperature of the filler particles may be determined through standard methods including differential scanning calorimetry or a melt point apparatus.

The composition may further comprise a plasticizing agent. Some examples of suitable plasticizing agents include water, polyethylene glycol with a molecular weight of 1,000 g/mol or lower, water, ethylene glycol, propylene glycol, diethylene glycol, and glycerin.

In one embodiment the three-dimensional object is a consumer product. Examples of consumer products include, baby care, beauty care, fabric & home care, family care, feminine care, health care products or devices intended to be used or consumed in the form in which it is sold, and is not intended for subsequent commercial manufacture or modification. Such products include but are not limited to: conditioners, hair colorants, body wash, shampoo, facial wash, and dish detergent for and/or methods relating to treating hair (human, dog, and/or cat), including bleaching, coloring, dyeing, conditioning, shampooing, styling; personal cleansing; cosmetics; skin care including application of creams, lotions, and other topically applied products for consumer use; and shaving products, products for and/or methods relating to treating fabrics, hard surfaces and any other surfaces in the area of home care, including: air care, car care, dishwashing, hard surface cleaning and/or treatment, and other cleaning for consumer or institutional use; products and/or methods relating to oral care including toothpastes, tooth gels, tooth rinses, denture adhesives, tooth whitening; over-the-counter health care including cough and cold remedies, pain relievers, pet health and nutrition, and water purification.

The composition may further comprise a benefit agent in addition to the filler particles and the polymer. The benefit agent may comprise: perfumes, pro-perfumes, finishing aids, malodor control and removal agents, odor neutralizers, polymeric dye transfer inhibiting agents builders, heavy metal ion sequestrants, surfactants, suds stabilizing polymers, dye fixatives, dye abrasion inhibitors, soil capture polymers, flocculating polymers, colorants, pigments, adversive agents such as bittering agents, anti-redeposition agents, bleach activators, bleach catalysts, bleach boosters, bleaches, photobleaches, enzymes, coenzymes, enzyme stabilizers, crystal growth inhibitors, anti-tarnishing agents, anti-oxidants, metal ion salts, corrosion inhibitors, antiperspirant, zinc pyrithione, plant derivatives, plant extracts, plant tissue extracts, plant seed extracts, plant oils, botanicals, botanical extracts, essential oils, skin sensates, astringents, etc. (e.g., clove oil, menthol, camphor, eucalyptus oil, eugenol, menthyl lactate, witch hazel distillate), anti-acne agents (salicylic acid), anti-dandruff agents, antifoaming agents, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), skin bleaching and lightening agents, (e.g., hydroquinone, kojic acid, ascorbic acid, magnesiuim ascorbyl phosphate, ascorbyl glucoside, pyridoxine), skin-conditioning agents (e.g., humectants and occlusive agents), skin soothing and/or healing agents and derivatives (e.g., panthenol, and derivatives such as ethyl panthenol, aloe vera, pantothenic acid and its derivatives, allantoin, bisabolol, and dipotassium glycyrrhizinate), skin treating agents (e.g., vitamin D compounds, mono-, di-, and tri-terpenoids, beta-ionol, cedrol), sunscreen agents, insect repellants, oral care actives, personal health care actives, vitamins, anti-bacterial agents, anti-microbial agents, anti-fungal agents, their derivatives, and mixtures thereof.

In one embodiment, the benefit agent is at least partially surrounded with a wall material to create a microcapsule. In one aspect, the microcapsule wall material may comprise: melamine, polyacrylamide, silicones, silica, polystyrene, polyurea, polyurethanes, polyacrylate based materials, gelatin, styrene malic anhydride, polyamides, and mixtures thereof. In one aspect, said melamine wall material may comprise melamine crosslinked with formaldehyde, melamine-dimethoxyethanol crosslinked with formaldehyde, and mixtures thereof. In one aspect, said polystyrene wall material may comprise polyestyrene cross-linked with divinylbenzene. In one aspect, said polyurea wall material may comprise urea crosslinked with formaldehyde, urea crosslinked with gluteraldehyde, and mixtures thereof. In one aspect, said polyacrylate based materials may comprise polyacrylate formed from methylmethacrylate/dimethylaminomethyl methacrylate, polyacrylate formed from amine acrylate and/or methacrylate and strong acid, polyacrylate formed from carboxylic acid acrylate and/or methacrylate monomer and strong base, polyacrylate formed from an amine acrylate and/or methacrylate monomer and a carboxylic acid acrylate and/or carboxylic acid methacrylate monomer, and mixtures thereof. In one aspect, the perfume microcapsule may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, and combinations thereof. In one aspect, one or more types of microcapsules, for example two microcapsules types having different benefit agents may be used.

In one embodiment, the benefit agent is a perfume oil and may include materials selected from the group consisting of 3-(4-t-butylphenyl)-2-methyl propanal, 3-(4-t-butylphenyl)-propanal, 3-(4-isopropylphenyl)-2-methylpropanal, 3-(3,4-methylenedioxyphenyl)-2-methylpropanal, and 2,6-dimethyl-5-heptenal, delta-damascone, alpha-damascone, beta-damascone, beta-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and □-dihydro ionone, linalool, ethyllinalool, tetrahydrolinalool, and dihydromyrcenol. Suitable perfume materials can be obtained from Givaudan Corp. of Mount Olive, N.J., USA, International Flavors & Fragrances Corp. of South Brunswick, N.J., USA, or Quest Corp. of Naarden, Netherlands. In one aspect, the benefit agent is a perfume microcapsule.

In one embodiment, the benefit agent is encapsulated in a shell. In one embodiment, the encapsulated benefit agent is perfume oil and the shell is a polymer.

In one embodiment the benefit agent is an enzyme. Suitable enzymes include proteases, amylases, cellulases, lipases, xylogucanases, pectate lyases, mannanases, bleaching enzymes, cutinases, and mixtures thereof.

For the enzymes, accession numbers or IDs shown in parentheses refer to the entry numbers in the databases Genbank, EMBL and Swiss-Prot. For any mutations standard 1-letter amino acid codes are used with a * representing a deletion. Accession numbers prefixed with DSM refer to microorgansims deposited at Deutsche Sammlung von Mikroorganismen and Zellkulturen GmbH, Mascheroder Weg 1b, 38124 Brunswick (DSMZ).

Protease. The composition may comprise a protease. Suitable proteases include metalloproteases and/or serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, Bacillus alkalophilus* (P27963, ELYA_BACAO), *Bacillus subtilis, Bacillus amyloliquefaciens* (P00782, SUBT_BACAM), *Bacillus pumilus* (P07518) and *Bacillus gibsonii* (DSM14391).

(b) trypsin-type or chymotrypsin-type proteases, such as trypsin (e.g. of porcine or bovine origin), including the *Fusarium* protease and the chymotrypsin proteases derived from *Cellumonas* (A2RQE2).

(c) metalloproteases, including those derived from *Bacillus amyloliquefaciens* (P06832, NPRE_BACAM).

Preferred proteases include those derived from *Bacillus gibsonii* or *Bacillus Lentus* such as subtilisin 309 (P29600) and/or DSM 5483 (P29599).

Suitable commercially available protease enzymes include: those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark); those sold under the tradename Maxatase®, Maxacal®, Maxapem®, Properase®, Purafect®, Purafect Prime®, Purafect Ox®, FN3®, FN4®, Excellase® and Purafect OXP® by Genencor International; those sold under the tradename Opticlean® and Optimase® by Solvay Enzymes; those available from Henkel/Kemira, namely BLAP (P29599 having the following mutations S99D+S101 R+S103A+V104I+G159S), and variants thereof including BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D) all from Henkel/Kemira; and KAP (*Bacillus alkalophilus* subtilisin with mutations A230V+S256G+S259N) from Kao.

Amylase: Suitable amylases are alpha-amylases, including those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCIB 12289, NCIB 12512, NCIB 12513, sp 707, DSM 9375, DSM 12368, DSMZ no. 12649, KSM AP1378, KSM K36 or KSM K38. Preferred amylases include:

(a) alpha-amylase derived from *Bacillus licheniformis* (P06278, AMY_BACLI), and variants thereof, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

(b) AA560 amylase (CBU30457, HD066534) and variants thereof, especially the variants with one or more substitutions in the following positions: 26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with the wild-type enzyme from Bacillus SP722 (CBU30453, HD066526), especially variants with deletions in the 183 and 184 positions.

Suitable commercially available alpha-amylases are Duramyl®, Liquezyme® Termamyl®, Termamyl Ultra®, Natalase®, Supramyl®, Stainzyme®, Stainzyme Plus®, Fungamyl® and BAN® (Novozymes A/S), Bioamylase® and variants thereof (Biocon India Ltd.), Kemzym® AT 9000 (Biozym Ges. m.b.H, Austria), Rapidase®, Purastar®, Optisize HT Plus®, Enzysize®, Powerase® and Purastar Oxam®, Maxamyl® (Genencor International Inc.) and KAM® (KAO, Japan). Preferred amylases are Natalase®, Stainzyme® and Stainzyme Plus®.

Cellulase: The composition may comprise a cellulase. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum*.

Commercially available cellulases include Celluzyme®, and Carezyme® (Novozymes A/S), Clazinase®, and Puradax HA® (Genencor International Inc.), and KAC-500 (B)® (Kao Corporation).

In one aspect, the cellulase can include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403), appended hereto as Sequence 1, and mixtures thereof. Suitable endoglucanases are sold under the tradenames Celluclean® and Whitezyme® (Novozymes A/S, Bagsvaerd, Denmark).

Preferably, the composition comprises a cleaning cellulase belonging to Glycosyl Hydrolase family 45 having a molecular weight of from 17 kDa to 30 kDa, for example the endoglucanases sold under the tradename Biotouch® NCD, DCC and DCL (AB Enzymes, Darmstadt, Germany).

Highly preferred cellulases also exhibit xyloglucanase activity, such as Whitezyme®.

Lipase. The composition may comprise a lipase. Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*), or from *H. insolens*, a *Pseudomonas* lipase, e.g., from *P. alcaligenes* or *P. pseudoalcaligenes, P. cepacia, P. stutzeri, P. fluorescens, Pseudomonas* sp. strain SD 705, *P. wisconsinensis*, a *Bacillus* lipase, e.g., from *B. subtilis, B. stearothermophilus* or *B. pumilus*.

The lipase may be a "first cycle lipase", preferably a variant of the wild-type lipase from *Thermomyces lanuginosus* comprising T231R and N233R mutations. The wild-type sequence is the 269 amino acids (amino acids 23-291) of the Swissprot accession number Swiss-Prot O59952 (derived from *Thermomyces lanuginosus* (*Humicola lanuginosa*)). Preferred lipases would include those sold under the tradenames Lipex®, Lipolex® and Lipoclean® by Novozymes, Bagsvaerd, Denmark.

Preferably, the composition comprises a variant of *Thermomyces lanuginosa* (O59952) lipase having >90% identity with the wild type amino acid and comprising substitution(s) at T231 and/or N233, preferably T231R and/or N233R.

In another aspect, the composition comprises a variant of *Thermomyces lanuginosa* (O59952) lipase having >90% identity with the wild type amino acid and comprising substitution(s):

(a) S58A+V60S+I83T+A150G+L227G+T231R+N233R+I255A+P256K;
(b) S58A+V60S+I86V+A150G+L227G+T231R+N233R+I255A+P256K;
(c) S58A+V60S+I86V+T143S+A150G+L227G+T231R+N233R+I255A+P256K;
(d) S58A+V60S+I86V+T143S+A150G+G163K+S216P+L227G+T231R+N233R+I255A+P256K;
(e) E1*+S58A+V60S+I86V+T143S+A150G+L227G+T231R+N233R+I255A+P256K;
(f) S58A+V60S+I86V+K98I+E99K+T143S+A150G+L227G+T231R+N233R+I255A+P256K;
(g) E1N+S58A+V60S+I86V+K98I+E99K+T143S+A150G+L227G+T231R+N233R+I255A+P256K+L259F;
(h) S58A+V60S+I86V+K98I+E99K+D102A+T143S+A150G+L227G+T231R+N233R+I255A+P256K;
(i) N33Q+S58A+V60S+I86V+T143S+A150G+L227G+T231R+N233R+I255A+P256K;
(j) E1*+S58A+V60S+I86V+K98I+E99K+T143S+A150G+L227G+T231R+N233R+I255A+P256K;
(k) E1N+S58A+V60S+I86V+K98I+E99K+T143S+A150G+S216P+L227G+T231R+N233R+I255A+P256K;
(l) D27N+S58A+V60S+I86V+G91N+N94R+D1 U N+T143S+A150G+L227G+T231R+N233R+I255A+P256K;
(m) E1N+S58A+V6OS+I86V+K98I+E99K+T143S+A150G+E210A+S216P+L227G+T231R+N233R+I255A+P256K;
(n) A150G+E210V+T231R+N233R+I255A+P256K; and
(o) I202L+E210G+T231R+N233R+I255A+P256K.

Xyloglucanase: Suitable xyloglucanase enzymes have enzymatic activity towards both xyloglucan and amorphous cellulose substrates, wherein the enzyme is a glycosyl hydrolase (GH) is selected from GH families 5, 12, 44 or 74. Preferably, the glycosyl hydrolase is selected from GH family 44. Suitable glycosyl hydrolases from GH family 44 are the XYG1006 glycosyl hydrolase from *Paenibacillus polyxyma* (ATCC 832) and variants thereof.

Pectate lyase: Suitable pectate lyases are either wild-types or variants of *Bacillus*-derived pectate lyases (CAF05441, AAU25568) sold under the tradenames Pectawash®, Pectaway® and X-Pect® (from Novozymes A/S, Bagsvaerd, Denmark).

Mannanase: Suitable mannanases are sold under the tradenames Mannaway® (from Novozymes A/S, Bagsvaerd, Denmark), and Purabrite® (Genencor International Inc., Palo Alto, Calif.).

Bleaching enzyme: Suitable bleach enzymes include oxidoreductases, for example oxidases such as glucose, choline or carbohydrate oxidases, oxygenases, catalases, peroxidases, like halo-, chloro-, bromo-, lignin-, glucose- or manganese-peroxidases, dioxygenases or laccases (phenoloxidases, polyphenoloxidases). Suitable commercial products are sold under the Guardzyme® and Denilite® ranges from Novozymes. Advantageously, additional, preferably organic, particularly preferably aromatic compounds are incorporated with the bleaching enzyme; these compounds interact with the bleaching enzyme to enhance the activity of the oxidoreductase (enhancer) or to facilitate the electron flow (mediator) between the oxidizing enzyme and the stain typically over strongly different redox potentials.

Other suitable bleaching enzymes include perhydrolases, which catalyse the formation of peracids from an ester substrate and peroxygen source. Suitable perhydrolases include variants of the Mycobacterium smegmatis perhydrolase, variants of so-called CE-7 perhydrolases, and variants of wild-type subtilisin Carlsberg possessing perhydrolase activity.

Cutinase: Suitable cutinases are defined by E.C. Class 3.1.1.73, preferably displaying at least 90%, or 95%, or most preferably at least 98% identity with a wild-type derived from one of *Fusarium solani, Pseudomonas Mendocina* or *Humicola Insolens*.

Identity. The relativity between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

In one embodiment, the three dimensional object comprises a container filled with one or more benefit agents. The container may be comprised at least partially from the materials of the invention to provide water solubility to at least a portion of the container to release the benefit agent. The benefit agent may comprise a single solid element, a collection of solid powder elements, a liquid or a gas. In one embodiment, the benefit agent may comprise a solid or powder and the benefit agent may enable the printing of a portion of the container directly in contact with the benefit agent, the benefit agent providing structural support for the printing, to close the container.

In one embodiment, the benefit agent is an oral care active. Suitable oral care actives include prevention agents including, but not limited to: sodium fluoride, stannous fluoride, sodium monofluorophosphate; dentinal hypersensitivity treatments including, but not limited to: potassium nitrate, strontium chloride and stannous fluoride; gingivitis prevention and treatment agents, including, but not limited to stannous fluoride, triclosan, cetyl pyridinium chloride and chlorhexidine; dental erosion prevention agents including, but not limited to: sodium fluoride, stannous fluoride and sodium polyphosphate; periodontitis treatment agents including, but not limited to chlorhexidine, tetracycline, doxycycline, and ketoprofen; dry mouth amelioration agents including, but not limited to pilocarpine, pellitorin.

In one embodiment, the benefit agent is a personal health care active. Suitable personal health care actives include Personal Healthe care: Cold and flu treatments including, but not limited to, Anti histamines, such as diphenhydramine hydrochloride, Doxylamine succinat, Chlorpheneramine Maleate, fexofenadine, terfenadine, cetirizine Decongestants; such as Phehylephrine Hydrochloride, Pseudoephedrine, Oxymetazoline, Expectorants, such as Guiafenesin, Cough Suppressants; such as dextromethorpand hydrobromide, Antipyretics and Analgesics, such as Acetaminophen, Ibuprofen, Naproxen, Aspirin. Antacids including but not limited to Acid reducers such as, magnesium Hydroxide, Alumimum Hydroxide, Calcium carbonate, Sodium bicarbonate, simethicone; H2 Antagonist, such as, cimetidine, ranitidine, famotidine; Proton Pump inhibitors, such as Omeprazole, Pantoprazole. Antidiarrheals including but not limited to bismuth subsalicylate, loperamide. Probiotics including but not limited to *Bifidobacterium infantis, Lactobacillus acidophilus*. Bulk forming fibers including but not limited to Psyllium.

Suitable fluorescent brighteners include: di-styryl biphenyl compounds, e.g. Tinopal® CBS-X, di-amino stilbene di-sulfonic acid compounds, e.g. Tinopal® DMS pure Xtra and Blankophor® HRH, and Pyrazoline compounds, e.g. Blankophor® SN, and coumarin compounds, e.g. Tinopal® SWN. Preferred brighteners are: sodium 2 (4-styryl-3-sulfophenyl)-2H-napthol[1,2-d]triazole, disodium 4,4'-bis{[4-anilino-6-(N methyl-N-2 hydroxyethyl)amino 1,3,5-triazin-2-yl)];amino}stilbene-2-2' disulfonate, disodium 4,4'-bis{[4-anilino-6-morpholino-1,3,5-triazin-2-yl)] amino}stilbene-2-2' disulfonate, and disodium 4,4'-bis(2-sulfostyryl)biphenyl. A suitable fluorescent brightener is C.I. Fluorescent Brightener 260, which may be used in its beta or alpha crystalline forms, or a mixture of these forms.

Preferred chelants are selected from: diethylene triamine pentaacetate, diethylene triamine penta(methyl phosphonic acid), ethylene diamine-N'N'-disuccinic acid, ethylene diamine tetraacetate, ethylene diamine tetra(methylene phosphonic acid) and hydroxyethane di(methylene phosphonic acid). A preferred chelant is ethylene diamine-N'N'-disuccinic acid and/or hydroxyethane diphosphonic acid.

Suitable hueing agents include small molecule dyes, typically falling into the Colour Index (C.I.) classifications of Acid, Direct, Basic, Reactive or hydrolysed Reactive, Solvent or Disperse dyes for example that are classified as Blue, Violet, Red, Green or Black, and provide the desired shade either alone or in combination. Preferred hueing agents include Acid Violet 50, Direct Violet 9, 66 and 99, Solvent Violet 13 and any combination thereof. Suitable hueing agents include phthalocyanine and azo dye conjugates, such as described in WO2009/069077.

The composition comprising the polymer and the filler particles has a Melt Flow Index (MFI) of between about 0.1 g/10 minutes and about 50 g/10 minutes when tested in accordance with ASTM D1238-13 under a 1.2 kg load at 70 C using a half die. Composition having MFIs outside this range either fail to flow adequately at 70 C under a 1.2 kg load using a half die, preventing their use in creating the actual voxels, or fail to be sufficiently dimensionally stable upon being extruded, resulting in a voxel error of unacceptable magnitude.

Voxel error relates to any change in dimensional requirements of a voxel due to expansion, shrinkage or movement of the material disposed for a particular voxel from the dimensional limits of that voxel. Voxel error magnitude for any particular may be calculated as the volume percent of the voxel which is missing at the time that the last voxel of the overall translation which is adjacent to the particular voxel, is deposited.

EXAMPLES

Example 1—Process for Making Polymer Blends

Mixtures are prepared by accurately weighing each component of the mixture into a glass jar at room temperature. The glass jars are capped and placed in an oven at a temperature above the melting temperature of the polymer and below the melting temperature of the filler (typical at 70 C), to the extent that the filler melts, for sufficient time to melt the polymer (typically two hours). The glass jars are removed from the oven and mixed to form a homogeneous blend. Any standard mixing technique that creates a homogeneous blend is sufficient. Examples of suitable mixing methods include stirring by hand with a spatula, overhead IKA mixers and a Flacktek SpeedMixer. Example mixtures are included in Tables 3 through 5 below where numbers represent printable mixtures and letters nonprintable mixtures.

Example 2—Time to Dissolve

Polymers and mixtures are melted by placing in an oven at a temperature above the melting temperature of the polymer and below the melting temperature of the filler. Typically samples are held at 70 C in sealed glass jars for 2 hours. The molten mixture is spread into triangular pyramid silicone molds where each triangular pyramid is symmetrical and 10 mm from base to opposite point. The mixture is cooled until solidified at room temperature. Each triangular pyramid is removed from the mold and weighed to ensure a weight of approximately 0.2 grams.

Time to dissolve is determined by placing a single triangular pyramid in a scintillation vial filled with approximately 20 grams of deionized water. The quiescent vial is backlit and imaged using time-lapse photography with one image taken every 30 seconds. The images are viewed sequentially as a movie at one frame per second. The time to dissolve is determined by eye as the time where the triangular pyramid is no longer visually apparent.

Example 3—FDM Printing of Mixtures

Polymers and mixtures are stored in sealed glass jars in an oven at 70 C until fully molten. Molten polymer and mixtures are transferred into a syringe fitted to a FDM printer. The syringe is preheated and can be mechanically or pneumatically driven. Polymers and mixtures can be 3D printed using a Hyrel 3D System 30M printer fitted with a VOL-25 extruder print head with a 0.5 mm circular tip and a Quiet Storm cooling fan. The computer aided design (CAD) files of the part to print is digitally sliced to create a STL file and transferred to the Hyrel 3D printer. Print conditions including syringe temperature and pneumatic syringe pressure are optimized for each polymer and mixture.

Example 4—Melt Flow Index

The Melt Flow Indexes are determined in accordance with ASTM D1238-13 at 70 C using a half die and a 1.2 kg load. The half die has a smooth straight bore 1.048±0.005 mm in diameter and is 4.000+/−0.025 mm in length. The set temperature is 70 C and the maximum allowable variation in temperature is +/−2 C measured 79+/−1 mm and +/−0.2 C measured 14 mm+/−1 mm above the die surface.

Example 5—Measuring Polymer Molecular Weight

The molecular weight of polyethylene glycol polymers and copolymers is measured using gel permeation chromatography with multi-angle light scattering and refractive index detectors (GPC-MALS/RI). Samples are prepared by dissolving 5 mg/ml of polymer in an aqueous solution of 0.1 M $NaNO_3$ M $NaNO_3$ and 0.02 weight percent sodium azide buffer. Samples are passed through a 0.45 micron syringe filter and analyzed separately by aqueous GPC-MALS/RI using the following conditions: Waters HPLC, 0.1 M $NaNO3$/0.02 weight percent sodium azide moble phase, two Waters Ultrahydragel columns (200 and 250) in tandem, each column 300×7.5 mm, column temperature of 40 C, and inject 50 microliters of 5 mg/ml polymer solution using isocratic flow at 1 ml/min. Polyethylene oxide standards available from Waters (24,000 Da to 850,000 Da) and Sigma (300 Da) are used for GPC calibration.

Data

Polymers suitable for melt rheology modification are described in Table 1. Polymers P2, P3 and P6 are printable without fillers. Polymer P1 and P5 are not dimensionally stable enough to hold shape during solidification and this leads to unacceptable voxel error. Polymer P4 does not flow at 70 C preventing the formation of actual voxels.

Fillers are described in Table 2. The particles all have a melt temperature greater than 75 C or degrade before melting.

A level study of fillers mixed with P1 is shown in Table 3. Polymer P1 alone is dimensionally unstable and cannot be printed. Mixture A contains fumed silica (RM1) as a filler but remains dimensionally unstable to be printable. The MFI is 59 g/10 minutes. Mixtures 1 through 5 are dimensionally stable and flow sufficiently to be printed and have MFI ranging between 0.1 g/10 minutes and 27 g/10 minutes. Mixtures 1 through 5 contain two types of fillers (silica F1 and F2); however, different levels are required to be printable. Mixtures B and C cannot be printed because they do not flow in the printer at 70 C. The MFI is 0 g/10 minutes.

Table 4 contains examples of other mixtures that are printable and not printable. Here, the unprintable compositions have a MFI of 0 g/10 minutes. The printable compositions have a MFI ranging from 1.3 g/10 minutes to 22 g/10 minutes.

Mixtures 11 and 12 contain both a filler and perfume oil as a benefit agent. These mixtures are printable with MFI of 11 g/10 minutes and 2.8 g/10 minutes, respectively.

The time to dissolve for each mixture varies with both the type and amount of filler. Time to dissolve for Polymer P1 is 1.6 hours (Table 1). Combining Polymer P1 with 2 wt. % and 4 wt. % filler silica F1 reduces the time to dissolve (Mixtures A and 1, respectively). Mixtures 2 and 3 contain 6 wt. % and 8 wt. % of silica F1 but the time to dissolve is slower than Polymer P1 alone. The same trend is observed for Mixtures 4 and 5 with Mixture 4 having a shorter time to dissolve and Mixture 5 having a longer time to dissolve than Polymer P1 alone. Table 4 illustrates that the type and level of filler has an unpredictable effect on the time to dissolve. This is further complicated in the presence of a benefit agent like perfume oil as noted in Table 5.

TABLE 1

Polymers P1-P6 studied for mixtures and comparative examples CE1 and CE2 that have a MFI that cannot be measured at 70 C. because the polymer does not melt or flow. Molecular weight is measured using gel permetation chromatography.

| Polymer # | Polymer Chemistry | Mn [g/mol] | PDI | Weight percent PEG | MFI [g/10 min] | Time to Dissolve [Hrs] | FDM Printable [Y/N] |
|---|---|---|---|---|---|---|---|
| P1 | PEG 8,000[1] | 7,300 | 1.2 | 100% | 99 | 1.6 | No |
| P2 | PEG 12,000[1] | 14,800 | 1.2 | 100% | 19 | 2.0 | Yes |
| P3 | PEG 35,000[1] | 34,600 | 1.3 | 100% | 1.4 | 2.7 | Yes |
| P4 | PEG 100,000[2] | 93,000 | 5.7 | 100% | 0 | 4.3 | No |
| P5 | PEG-PPO-PEG[3] | 1,500 | 1.1 | 50% | >100[7] | 3.2 | No |
| P6 | PEG-PPO-PEG[4] | 1,700 | 9.7 | 70% | 40 | 7.2 | Yes |
| CE1 | Poly(2-ethyl-2-oxazoline)[5] | Not Measured | Not Measured | 0% | 0[8] | Not Measured | Not Tested |
| CE2 | Polyvinyl alcohol[6] | Not Measured | Not Measured | 0% | 0[8] | Not Measured | Not Tested |

[1]Poly(ethylene glycol) supplied by SigmaAldrich
[2]Polyox WSR N10 from Dow Chemical
[3]Poly(ethylene glycol-block-propylene oxide-block-ethylene glycol) sold under the trade name Pluronic P105 from BASF®
[4]Poly(ethylene glycol-block-propylene oxide-block-ethylene glycol) sold under the trade name Pluronic F-127 from BASF®
[5]Supplied by Alfa Aesar molecular weight target 50,000 g/mol
[6]Poly(vinyl alcohol) 98% hydrolyzed from SigmaAldrich target MW 13,000 to 23,000 g/mol
[7]Polymer flowed through dye without weight before experiment could begin
[8]Polymer does not melt or flow at 70° C.

TABLE 2

Melting temperature of fillers.

| Fillers | Particle Type | Melting Temperature[1] [° C.] |
|---|---|---|
| F1 | Fumed Silica[2] | N/A[4] |
| F2 | Silica[3] | N/A[4] |
| F3 | Corn Starch[2] | N/A[4] |
| F4 | D-Mannitol[2] | 167-170 |
| F5 | Xanthan gum[2] | N/A[4] |
| F6 | Sodium dodecylbenzene sulfonate[2] | >300 |
| F7 | Sucrose[2] | 186 |

[1]Melting temperature obtained from safety data sheet
[2]Supplied from SigmaAldrich
[3]Supplied from Huber
[4]Melting temperature unavailable. Particles burn or decompose before melting.

TABLE 3

Level study of fillers F1 & F2 with polymer P1, the mixture MFI, time to dissolve and evaluation of FDM printability.

| Mixture | Polymer Type | Wt. % | Filler Type | Wt. % | MFI @ 70° C. [g/10 min] | Time to Dissolve [Hrs] | FDM Printable [Yes/No] |
|---|---|---|---|---|---|---|---|
| A | P1 (PEG 8k) | 98 | F1 (F. Silica) | 2 | 59 | 1.0 | No |
| 1 | P1 (PEG 8k) | 96 | F1 (F. Silica) | 4 | 27 | 1.1 | Yes |
| 2 | P1 (PEG 8k) | 94 | F1 (F. Silica) | 6 | 12 | 2.5 | Yes |
| 3 | P1 (PEG 8k) | 92 | F1 (F. Silica) | 8 | 0.2 | 6.6 | Yes |
| B | P1 (PEG 8k) | 90 | F1 (F. Silica) | 10 | 0.0 | 16.3 | No |
| 4 | P1 (PEG 8k) | 70 | F2 (Silica) | 30 | 11.5 | 1.0 | Yes |
| 5 | P1 (PEG 8k) | 60 | F2 (Silica) | 40 | 0.1 | 2.8 | Yes |
| C | P1 (PEG 8k) | 50 | F2 (Silica) | 50 | 0.0 | N/A[1] | No |

[1]Did not flow enough to be formed into triangle based pyramids used for dissolution testing

TABLE 4

Mixtures of polymers and fillers their respective MFI, time to dissolve and if the mixture is FDM printable.

| Mixture | Polymer Type | Wt. % | Fillers Type | Wt. % | MFI @ 70° C. [g/10 min] | Time to Dissolve [hrs] | FDM Printable [Yes/No] |
|---|---|---|---|---|---|---|---|
| D | P1 (PEG 8k) | 50 | F5 (x-gum) | 50 | 0.0 | >40 | No |
| E | P1 (PEG 8k) | 50 | F7 (Sucrose) | 50 | 0.0 | 0.7 | No |
| 6 | P1 (PEG 8k) | 55 | F6 (SDBS) | 45 | 12 | 0.4 | Yes |
| 7 | P2 (PEG 12k) | 40 | F3 (C. Starch) | 60 | 1.5 | 4.8 | Yes |
| 8 | P2 (PEG 12k) | 50 | F3 (C. Starch) | 20 | 2.3 | 1.2 | Yes |
|   |   |   | F4 (Mannitol) | 30 |   |   |   |
| 9 | P5 (P105) | 50 | F4 (Mannitol) | 50 | 22 | 1.6 | Yes |
| 10 | P6 (F127) | 60 | F2 (Silica) | 40 | 1.3 | 2.3 | Yes |

TABLE 5

Mixtures of polymer, filler and perfume oil

| Mixture | Polymer Type | Wt. % | Fillers Type | Wt. % | Perfume Oil Wt. % | MFI @ 70 C. [g/10 min] | Time to Dissolve [hrs] | FDM Printable [Yes/No] |
|---|---|---|---|---|---|---|---|---|
| 11 | P1 (PEG 8k) | 90 | F1 (F. Silica) | 8 | 2 | 11 | 1.4 | Yes |
| 12 | P2 (PEG 12k) | 53 | F6 (SDBS) | 45 | 2 | 2.8 | 0.7 | Yes |

TABLE 6

Printing temperature and pressure for polymers and mixtures

| Polymer or Mixture | Print Temperature [C.] | Print Pressure [PSI] |
|---|---|---|
| P2 | 60 | 8-10 |
| P3 | 75 | 20-25 |
| P6 | 60 | 10-12 |
| 1 | 60 | 8 |
| 2 | 51 | 10 |
| 3 | 75 | 44 |
| 5 | 75 | 40 |
| 11 | 60 | 20 |
| 12 | 63 | 100 |
| 8 | 57 | 45 |
| 6 | 65 | 100 |
| 7 | 75 | 15-45 |
| 10 | 75 | 30-45 |
| 9 | 60 | 18 |

A. A filament composition comprising between about 35 and about 100 wt. % of a polymer selected from the group consisting of nonionic polyethylene glycol (PEG) homopolymers, PEG copolymers, and mixtures thereof; the polymer having an average molecular weight of between about 1,000 and about 95,000 AMU; and between about 0 and about 65 wt. % of a filler, wherein the filler is a solid at a temperature of above about 70 C, wherein the composition has a Melt Flow Index of between about 0.1 and about 50 g/10 min at 70 C under a 1.2 kg load.

B. The filament according to paragraph A wherein the polymer comprises at least about 50% PEG.

C. The filament according to any of paragraphs A or B, wherein the composition further comprises a benefit agent selected from the group consisting of: builders, surfactants, bleach activators, bleach catalysts, bleach boosters, bleaches, alkalinity sources, antibacterial agents, colorants, perfumes, pro-perfumes, finishing aids, composition malodor control and removal agents, odor neutralizers, polymeric dye transfer inhibiting agents, crystal growth inhibitors, photobleaches, heavy metal ion sequestrants, anti-tarnishing agents, anti-microbial agents, anti-oxidants, anti-redeposition agents, electrolytes, divalent or trivalent ions, metal ion salts, corrosion inhibitors, diamines, diamine alkoxylates, polyamines alkoxylates, suds stabilizing polymers, solvents, process aids dye fixatives, dye abrasion inhibitors, sunscreen agents, insect repellants, bittering agents, antiperspirant and mixtures thereof.

D. The filament according to paragraphs A, B, or C, wherein the composition comprises between about 35 and about 99 wt. % of a polymer selected from the group consisting of nonionic PEG homopolymers, PEG copolymers, and mixtures thereof; the polymer having an average molecular weight of between about 1,000 and about 95,000 AMU; and between about 1 and about 65 wt. % of a filler, wherein the filler is a solid at a temperature of above about 70 C, wherein the composition has a Melt Flow Index of between about 0.1 and about 50 g/10 min at 70 C under a 1.2 kg load.

E. A method for manufacturing a three-dimensional object, the method comprising steps of:

a) providing a digital description of the object as a set of voxels;

b) sequentially creating an actual set of voxels corresponding to the digital set of voxels;

wherein at least one voxel comprises a composition comprising between about 35 and about 100 wt. % of a polymer selected from the group consisting of nonionic PEG homopolymers, PEG copolymers, and mixtures thereof; the polymer having an average molecular weight of between about 1,000 and about 95,000 AMU; and between about 0 and about 65 wt. % of a filler, wherein the filler is a solid at a temperature of above about 70 C, wherein the composition has a Melt Flow Index of between about 0.1 and about 50 g/10 min at 70 C under a 1.2 kg load.

F. The method according to paragraph E, wherein the polymer comprises at least about 50% PEG.

G. The method according to any one of paragraphs E, or F, wherein the composition further comprises a benefit agent selected from the group consisting of: builders, surfactants, bleach activators, bleach catalysts, bleach boosters, bleaches, antibacterial agents, colorants, perfumes, pro-perfumes, finishing aids, composition malodor control and removal agents, odor neutralizers, crystal growth inhibitors, photobleaches, heavy metal ion sequestrants, anti-tarnishing agents, anti-microbial agents, anti-oxidants, electrolytes, divalent or trivalent ions, metal ion salts, corrosion inhibitors, suds stabilizing polymers, solvents, process aids, fixatives, dye abrasion inhibitors, sunscreen agents, insect repellants, bittering agents, antiperspirant and mixtures thereof.

H. The method according to any of paragraphs E, F, or G, wherein the three-dimensional object is a consumer product.

I. The method according to any of paragraphs E, F, G, or H, wherein the object comprises a hollow shell.

J. The method according to any of paragraphs E, F, G, H, or I, wherein the composition comprises between about 35 and about 99 wt. % of a polymer selected from the group consisting of nonionic PEG homopolymers, PEG copolymers, and mixtures thereof; the polymer having an average molecular weight of between about 1,000 and about 95,000 AMU; and between about 1 and about 65 wt. % of a filler, wherein the filler is a solid at a temperature of above about 70 C, wherein the composition has a Melt Flow Index of between about 0.1 and about 50 g/10 min at 70 C under a 1.2 kg load K. An article comprising a composition, the composition comprising between about 35 and about 100 wt. % of a polymer selected from the group consisting of nonionic PEG homopolymers, PEG copolymers, and mixtures thereof; the polymer having an average molecular weight of between about 1,000 and about 95,000 AMU; and between about 0 and about 65 wt. % of a filler, wherein the filler is a solid at a temperature of above about 70 C, wherein the composition has a Melt Flow Index of between about 0.2 and about 20 g/10 min at 70 C under a 1.2 kg load.

L. The article according to paragraph K, wherein the polymer comprises at least about 50% PEG.

M. The article according to any of paragraphs K, or L, wherein the composition further comprises a benefit agent selected from the group consisting of: builders, surfactants, bleach activators, bleach catalysts, bleach boosters, bleaches, antibacterial agents, colorants, perfumes, pro-perfumes, finishing aids, composition malodor control and removal agents, odor neutralizers, polymeric dye transfer inhibiting agents, crystal growth inhibitors, photobleaches, heavy metal ion sequestrants, anti-tarnishing agents, anti-microbial agents, anti-oxidants, anti-redeposition agents, electrolytes, divalent or trivalent ions, metal ion salts, corrosion inhibitors, suds stabilizing polymers, solvents, process aids, sunscreen agents, insect repellants, bittering agents, antiperspirant and mixtures thereof.

N. The article according to any of paragraphs K, L, or M, wherein the article is a consumer product.

O. The article according to any of paragraphs K, L, M, or N, wherein the article comprises a hollow shell.

P. A method for manufacturing a three-dimensional object, the method comprising steps of:
 a) providing a digital description of the object as a set of voxels;
 b) sequentially creating an actual set of voxels corresponding to the digital set of voxels;
 wherein at least one voxel comprises a composition comprising between about 35 and about 100 wt. % of a polymer selected from the group consisting of nonionic PEG homopolymers, PEG copolymers, and mixtures thereof; the polymer having an average molecular weight of between about 1,000 and about 95,000 AMU; and between about 0 and about 65 wt. % of a filler, wherein the filler is a solid at a temperature of above about 70 C, wherein the composition has a Melt Flow Index of between about 0.1 and about 50 g/10 min when measured at 70 C under a 1.2 kg load using a half-die according to ASTM D1238-13.

Q. The method according to paragraph P, wherein the polymer comprises at least about 50 weight percent PEG.

R. The method according to any of paragraphs P, or Q, wherein the printing temperature is less than 100 C.

S. The method according to any of paragraphs P, Q, or R, wherein the composition further comprises a benefit agent selected from the group consisting of: builders, surfactants, bleach activators, bleach catalysts, bleach boosters, bleaches antibacterial agents, colorants, perfumes, pro-perfumes, finishing aids, composition malodor control and removal agents, odor neutralizers, crystal growth inhibitors, photobleaches, heavy metal ion sequestrants, anti-tarnishing agents, anti-microbial agents, anti-oxidants, electrolytes, divalent or trivalent ions, metal ion salts, corrosion inhibitors, solvents, process aids sunscreen agents, insect repellants, bittering agents, antiperspirant and mixtures thereof.

T. The method according to any of paragraphs P, Q, R, or S, wherein the three-dimensional object is a consumer product.

U. The method according to any of paragraphs P, Q, R, S, or T, wherein the benefit agent is encapsulated in a shell.

V. The method according to any of paragraphs P, Q, R, SA, T, or U, wherein the composition comprises between about 35 and about 99 wt. % of a polymer selected from the group consisting of nonionic PEG homopolymers, PEG copolymers, and mixtures thereof; the polymer having an average molecular weight of between about 1,000 and about 95,000 AMU; and between about 1 and about 65 wt. % of a filler, wherein the filler is a solid at a temperature of above about 70 C, wherein the composition has a Melt Flow Index of between about 0.1 and about 50 g/10 min when measured at 70 C under a 1.2 kg load using a half-die according to ASTM D1238-13.

W. The method according to any of paragraphs P, Q, R, S, T, U, or V, wherein the filler is spherical in shape.

X. The method according to any of paragraphs P, Q, R, S, T, U, V, or W, wherein the composition comprises between about 0.1 and about 10% by weight of a perfume composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing a three-dimensional water-soluble consumer product comprising an actual set of voxels, the method comprising the steps of:
   a. providing a digital description of the product as a set of voxels;
   b. sequentially 3D printing, the actual set of voxels corresponding to the digital set of voxels;
   wherein at least one voxel comprises:
   from about 40 wt % to about 96 wt % of a water-soluble polymer composition comprising a molecular weight from about 1000 to about 95000 AMU;
   wherein the water-soluble polymer is selected from the group consisting of nonionic PEG homopolymers, PEG copolymers, and mixtures thereof;
   from about 1 wt % to about 65 wt % of a filler comprising a melt temperature greater than about 75° C. and wherein the filler is solid at a temperature greater than the melting and printing temperature of the at least one voxel;
   wherein the filler comprises an organic material selected from the group consisting of starches, gums, proteins, amino acids, water soluble polymers, water degradable polymers, water insoluble polymers, sugars, sugar alcohols, surfactants, fatty amphiphiles and mixtures thereof;
   wherein the filler further comprises a benefit agent selected from the group consisting of builders, surfactants, bleach activators, bleach catalysts, bleach boosters, bleaches, antibacterial agents, colorants, perfumes, pro-perfumes, composition malodor control and removal agents, odor neutralizers, polymeric dye transfer inhibiting agents, crystal growth inhibitors, photobleaches, heavy metal ion sequestrants, anti-tarnishing agents, anti-microbial agents, anti-oxidants, anti-redeposition agents, electrolytes, divalent or trivalent ions, metal ion salts, corrosion inhibitors, suds stabilizing polymers, solvents, process aids, dye fixatives, dye abrasion inhibitors, sunscreen agents, insect repellants, bittering agents, antiperspirant and mixtures thereof;
   wherein the water-soluble consumer product is selected from the group consisting of conditioners, hair colorants, body wash, shampoo, facial wash, dish detergent, personal cleansing, skin care products, shaving products, fabric care products, hard surface cleansers, air care products, oral care products, over-the-counter health care products, and combinations thereof.

2. The method of claim 1, wherein the consumer product is selected from the group consisting of body wash, shampoo, facial wash, dish detergent; hard surface cleansers; fabric care products; and shaving products.

3. The method of claim 2, wherein the benefit agent comprises a surfactant.

4. The method of claim 3, wherein the benefit agent further comprises a perfume.

5. The method of claim 3, wherein the consumer product is a fabric care product.

6. The method of claim 1, wherein the at least one voxel comprises from about 50 wt % to about 94 wt % of the water-soluble polymer.

7. The method of claim 6, wherein the at least one voxel comprises from about 55 wt % to about 92 wt % of the water-soluble polymer.

8. The method of claim 1, wherein the at least one voxel comprises from about 6 wt % to about 50 wt % of the filler.

9. The method of claim 8, wherein the at least one voxel comprises from about 8 wt % to about 45 wt % of the filler.

10. The method of claim 1, wherein the water-soluble consumer product comprises a Melt Flow Index of between about 0.1 and about 50 g/10 min when measured at 70 C under a 1.2 kg load using a half-die according to ASTM D1238-13.

11. A method of manufacturing a three-dimensional water-soluble consumer product comprising an actual set of voxels, the method comprising the steps of:
   a. providing a digital description of the product as a set of voxels;
   b. sequentially 3D printing, the actual set of voxels corresponding to the digital set of voxels;
   wherein at least one voxel comprises:
   from about 40 wt % to about 96 wt % of a water-soluble polymer composition comprising a molecular weight from about 1000 to about 95000 AMU;
   wherein the water-soluble polymer is selected from the group consisting of nonionic PEG homopolymers, PEG copolymers, and mixtures thereof;
   from about 1 wt % to about 65 wt % of a filler comprising a melt temperature greater than about 75° C. and wherein the filler is solid at a temperature greater than the melting and printing temperature of the at least one voxel;
   wherein the water-soluble consumer product is selected from the group consisting of conditioners, hair colorants, body wash, shampoo, facial wash, dish detergent, personal cleansing, skin care products, shaving products, fabric care products, hard surface cleansers, air care products, oral care products, over-the-counter health care products, and combinations thereof.

12. The method of claim 11, wherein the water-soluble consumer product comprises a Melt Flow Index of between about 0.1 and about 50 g/10 min when measured at 70 C under a 1.2 kg load using a half-die according to ASTM D1238-13.

13. The method of claim 11, wherein the filler is organic and is selected from the group consisting of starches, gums, proteins, amino acids, water soluble polymers, water degradable polymers, water insoluble polymers, sugars, sugar alcohols, surfactants, fatty amphiphiles and mixtures thereof.

14. The method of claim 13, wherein the filler further comprises a benefit agent selected from the group consisting of builders, surfactants, bleach activators, bleach catalysts, bleach boosters, bleaches, antibacterial agents, colorants, perfumes, pro-perfumes, composition malodor control and removal agents, odor neutralizers, polymeric dye transfer inhibiting agents, crystal growth inhibitors, photobleaches, heavy metal ion sequestrants, anti-tarnishing agents, anti-microbial agents, anti-oxidants, anti-redeposition agents, electrolytes, divalent or trivalent ions, metal ion salts, corrosion inhibitors, suds stabilizing polymers, solvents, process aids, dye fixatives, dye abrasion inhibitors, sunscreen agents, insect repellants, bittering agents, antiperspirant and mixtures thereof.

15. The method according to claim 14 wherein the benefit agent is encapsulated in a shell.

* * * * *